United States Patent [19]

Sven

[11] Patent Number: 5,247,218

[45] Date of Patent: Sep. 21, 1993

[54] HAND HELD VIBRATING INSTRUMENT

[76] Inventor: J. Eric Sven, 4320 322nd St., Federal Way, Wash. 98023

[21] Appl. No.: 896,375

[22] Filed: Jun. 10, 1992

[51] Int. Cl.$^5$ .................. H02K 11/00; H02K 7/075
[52] U.S. Cl. ................................. 310/81; 310/68 A
[58] Field of Search ............ 310/89, 81, 50, 68 A; 433/118, 122; 200/332.2

[56] References Cited

U.S. PATENT DOCUMENTS

| | | | |
|---|---|---|---|
| 3,685,080 | 8/1972 | Hubner | 15/22 R |
| 3,783,364 | 1/1974 | Gallanis et al. | 320/2 |
| 4,561,214 | 12/1985 | Inoue | 51/165 R |
| 5,044,356 | 9/1991 | Fishman et al. | 128/62 A |
| 5,123,841 | 6/1992 | Millner | 433/125 |
| 5,145,369 | 9/1992 | Lustig et al. | 433/118 |

Primary Examiner—Steven L. Stephan
Assistant Examiner—D. R. Haszko
Attorney, Agent, or Firm—Jack C. Munro

[57] ABSTRACT

A hand held vibrating instrument in the shape of a conventional pen or pencil writing instrument. The tip of this instrument is to be connected to a tool such as a thin brush. The instrument has a deflectable sleeve mounted within the housing wall of the instrument. Manual inward deflecting of the sleeve will cause operation of a motor which will rotate an eccentric weight and cause rapid vibration of the brush.

3 Claims, 1 Drawing Sheet

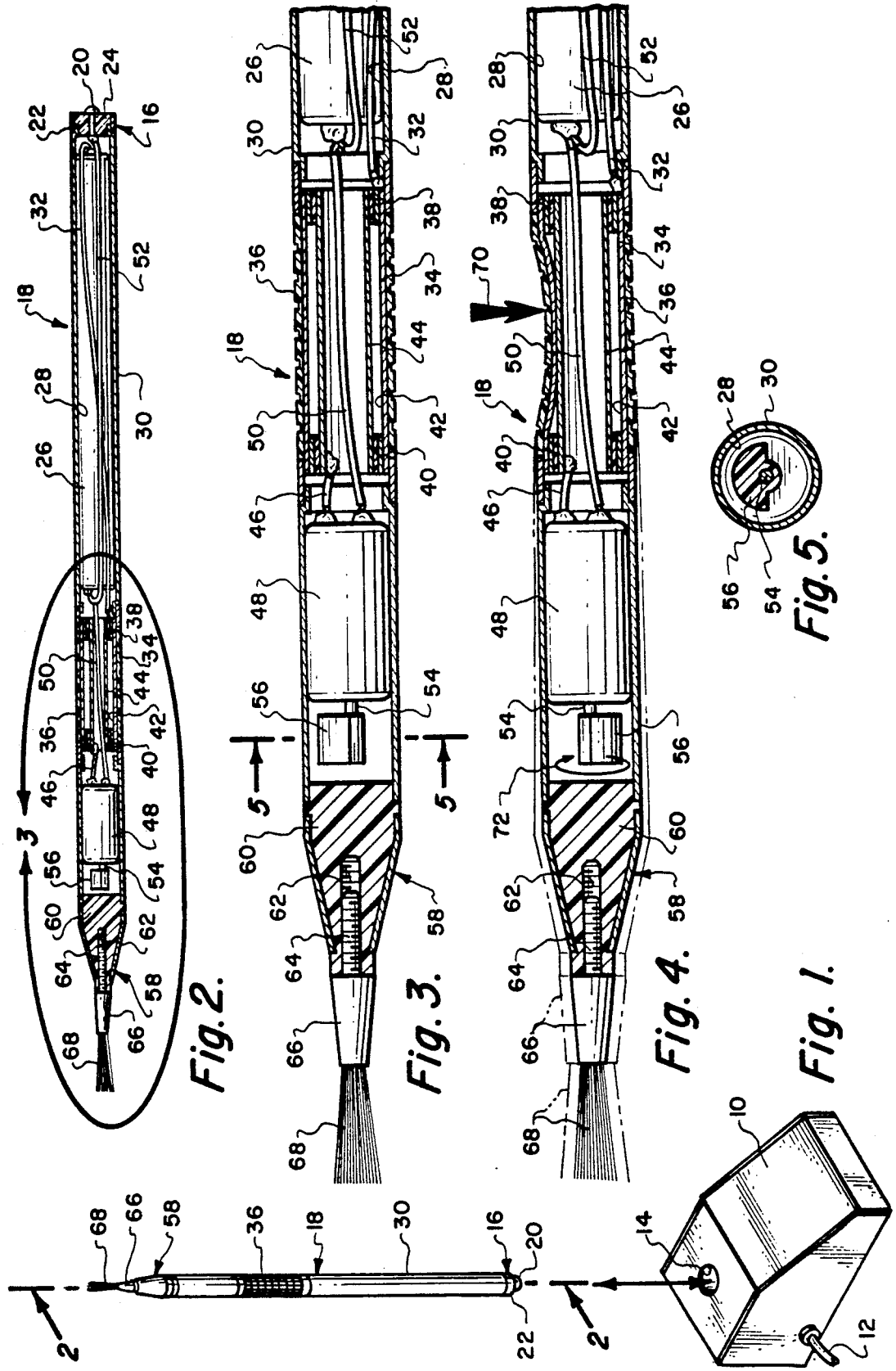

HAND HELD VIBRATING INSTRUMENT

BACKGROUND OF THE INVENTION

1) Field of the Invention

The field of this invention relates to a hand held instrument which is in the shape of a conventional writing instrument such as a pen or pencil, the instrument having a tip in the shape of a tool such as a thin brush.

2) Description of the Prior Art

The subject matter of this invention has been found to be of particular utility in the dental field particularly in the manufacture of dental crowns and fixed bridges. However, it is considered to be within the scope of this invention that the instrument of the present invention could be utilized in numerous other fields. Additionally, the instrument of the present invention is described in the configuration of a brush. However, it is considered to be within the scope of this invention that the instrument could be in a configuration of numerous other tools other than a brush.

In the manufacture of dental devices, there is a need to apply a layer of porcelain material which will be applied in a liquid slurry state and then permitted to dry. The dried dental device is then baked into a solid hard configuration. It is very important that the application be smooth, precise, of constant thickness and to be attractive in appearance and not having a pattern with the appearance being smooth. It is common that, in order to achieve such a smooth, consistent and attractive application, there is utilized a small brush. It has further been found that if this small brush could be vibrated then the application of this liquid material is enhanced.

The prior art type of vibrating brush is connected by a wire to a source of electrical power. The fact that the brush has an electrical wire tethered to it significantly affects the mobility of the brush and especially in tight quartered situations where one is trying to apply an even smooth coating of material. Also, the prior art of brush is about an inch in diameter which proves to be too large to hold by a technician for any extended length of time. Further, the prior art brush is quite noisy which quickly becomes annoying to the technician. Still further, a foot is needed to operate the brush which makes the brush possibly not usable by handicapped people.

If a vibrating brush could be constructed that would not have an electrical conducting wire and this brush still had the basic overall configuration of a conventional hand held writing instrument such as a pen or pencil, then the usage of this instrument would be enhanced especially in tight quartered situations. Within the dental field, such an instrument could result in creating a most attractive dental product in the minimum amount of manufacturing time.

SUMMARY OF THE INVENTION

The structure of the present invention comprises a hand held type of instrument that has an elongated, thin housing which terminates in a tool type of tip such as a small thin brush. Included within the housing is a small motor which when activated will cause the brush to rapidly vibrate. Included within the housing is a deflectable sleeve with this deflectable sleeve being located in the area where the user's fingers would be normally located when using the instrument. Applying a slight pressure onto the sleeve will result in vibration of the brush. Within the aft end of the housing is an electrical connection which is to permit the brush to be mounted within a recharging stand for recharging of a battery incorporated within the housing.

The primary objective of the present invention is to construct a vibrating instrument where the instrument does not require any type of connection to an electrical wire when it is being used, therefore being cordless.

Another objective of the present invention is to construct a vibrating instrument which is small in diameter resembling in configuration a conventional writing instrument, about one-third the diameter of the conventional (prior art) vibrating brush.

Another objective of the present invention is to construct a hand held vibrating instrument where the vibration of the instrument can be quickly and easily activated and deactivated without requiring changing of the position of the user's hands on the instrument and which does not require a foot pedal for activation.

Another objective of the present invention is to construct a silent vibrating instrument.

BRIEF DESCRIPTION OF THE DRAWINGS

FIG. 1 is an isometric view of the hand held vibrating instrument of the present invention showing its association with a recharging stand;

FIG. 2 is a longitudinal cross sectional view through the writing instrument of the present invention taken along line 2—2 of FIG. 1;

FIG. 3 is an enlarged cross-sectional view similar to that of FIG. 2 taken along line 3—3 of FIG. 2 showing the position of the instrument when it is not activated;

FIG. 4 is a view similar to FIG. 3 but showing the position of the instrument when it is vibrating; and FIG. 5 is a transverse, cross-sectional view through the instrument of the present invention taken along line 5—5 of FIG. 3.

DETAILED DESCRIPTION OF THE SHOWN EMBODIMENT

Referring particularly to the drawings there is shown a recharging stand 10 which is to be connected to an electrical source by an electrical connecting wire 12. The stand 10 includes a hole 14. Within the hole 14 there is to be located the aft end 16 of the vibrating instrument 18 of the present invention. The aft end 16 includes a positive electrical connector 20 and a negative electrical connector 22. The electrical connector 22 is in the form of a collar mounted around a plug 24 within which is centrally mounted a positive electrical connector 20. The connectors 20 and 22 are to connect with an appropriate electrical connection within the hole 14 so as to provide a continuous stream of recharging electrical current through appropriate wire connections to recharge battery 26. Battery 26 is mounted within internal chamber 28 of housing 30. The housing 30 will be normally constructed of a thin walled cylindrically tubular structure which could either be metal or plastic. The negative side of the battery 26 is connected through conductor 32 to an outer conducting sleeve 34. Surrounding the sleeve 34 and mounted in a closely conforming relationship thereto is a rubber sleeve 36.

The ends of the sleeve 34 are interiorly supported by insulative collars 38 and 40. Between the collars 38 and 40 is an annular space 42. Supported between the collars 38 and 40 and located interiorly thereof is an inner sleeve 44. The inner sleeve 44 is electrically connected by a wire 46 to a motor 48. Motor 48 is mounted within the internal chamber 28. The motor 48 is also electrically connected by wire 50 to the positive side of the battery 26. To the positive side of battery 26 there is a wire 52 that connects to the positive electrical connector 20. The wire 52 is utilized in order to affect the recharging of the instrument 18.

The motor 48 has a rotatable output shaft 54. This shaft 54 has mounted thereon a weight 56. It is to be noted that the weight 56 is eccentrically mounted on the shaft 54.

The fore end 58 of the writing instrument 18 includes a plug 60 mounted within the internal chamber 28 of the fore end 58. Plug 60 includes a threaded hole 62. The hole 62 is to threadably connect with a threaded rod 64. The threaded rod 64 is fixedly mounted on a ferrule 66. The ferrule 66 supports the bristles 68.

The instrument 18 can be grasped by the user with the hands of the user being located in the area of the rubber sleeve 36. The user is capable of using the instrument 18 by applying of the bristles 68 onto an exterior structure (not shown) with the instrument being used as a conventional brush.

If the user wishes to cause the bristles 16 to vibrate as is depicted in phantom lines within FIG. 4 of the drawing, the user only needs to apply a slight pressure onto the rubber sleeve 36 inwardly depressing such in the direction of arrow 70. This deflection will cause the outer conducting sleeve 34 to be moved inwardly and come into contact with the inner sleeve 44. An electrical connection therebetween is produced which electrically connects the motor 48 to the battery 26. Shaft 54 of the motor 48 is rotated which in turn causes the weight 56 to rotate as is depicted by arrow 72. This rotation of the weight 56 produces a rapid vibration of the bristles 68 which will then facilitate the application of the liquid material (not shown) which is contained within the bristles 68 onto the exterior structure (not shown). Release of the manual pressure on the rubber sleeve 36 will cause the sleeve 36 to be moved back to the position shown in FIG. 3 which will again cause the sleeves 34 and 44 to separate which will result in deactivation of the motor 48.

It is to be understood that the sleeve 36 can be depressed for an extended period of time or can be depressed sporadically at short intervals. Deactivation of the vibrating brush 18 of this invention is strictly at the choice of the user.

What is claimed is:

1. A hand held vibrating instrument comprising:

an elongated housing for grasping to be used in the hand of a human similar to a conventional pen or pencil writing instrument, said elongated housing having an internal chamber and a fore end and an aft end;

connecting means mounted on said fore end for connection to a tool such as a brush;

motor means for rotating said tool, said motor means being mounted within said internal chamber, said motor means including a rotatable shaft, a weight eccentrically mounted on said shaft, the rotation of said shaft rotates said weight and produces a rapid vibration at said fore end;

battery means mounted within said internal chamber, said battery means for providing electrical energy to operate said motor means; and switch means for controlling operation of said motor means, said switch means being mounted on said housing, said switch means being moveable between an activating position and a deactivating position, with said switch means in said activating position said motor means is operated with said switch means in said deactivating position said motor means is not operated, said switch means being in said deactivating position when at rest, said switch means being manually pressable by the human to be moved to said activating position, said switch means includes a deflectable sleeve where a deflection of said deflectable sleeve places said switch mean sin said activating position, said deflectable sleeve having an exterior wall, said housing having an exterior wall surface, said exterior wall of said deflectable sleeve is in alignment with said exterior wall surface of said housing.

2. The hand held vibrating instrument as defined in claim 1 wherein:

said deflectable sleeve is located nearer said fore end than said aft end.

3. The hand held vibrating instrument as defined in claim 2 wherein:

said aft end includes a pair of electrical connections, said electrical connections to be used to recharge said battery means.

* * * * *